:::

United States Patent
Berghaus et al.

(12) 
(10) Patent No.: US 6,225,259 B1
(45) Date of Patent: May 1, 2001

(54) LIQUID FORMULATION OF ETHYL-(Z)-2-CHLORO-3-[2-CHLORO-5-(4,5,6,7-TETRAHYDRO-1,3-DIOXOISOINDOLEDION-2-YL)PHENYL]ACRYLATE

(76) Inventors: Rainer Berghaus, Rotkehlchenweg 25, 67346 Speyer; Dieter Kleuser, Pierstr. 4, 67227 Frankenthal; Matthias Bratz, Sachsenweg 10, 67117 Limburgerhof; Adolf Parg, Paray-Le-Monial-Str. 8, 67098 Bad Dürkheim; Wessel Nuyken, Keltenstr.1, 67166 Otterstadt, all of (DE)

( * ) Notice: Subject to any disclaimer, the term of this patent is extended or adjusted under 35 U.S.C. 154(b) by 0 days.

(21) Appl. No.: 09/242,125

(22) PCT Filed: Aug. 5, 1997

(86) PCT No.: PCT/EP97/04253

§ 371 Date: Dec. 3, 1999

§ 102(e) Date: Dec. 3, 1999

(87) PCT Pub. No.: WO98/07319

PCT Pub. Date: Feb. 26, 1998

(30) Foreign Application Priority Data

Aug. 19, 1996 (DE) ................................. 196 33 271

(51) Int. Cl.$^7$ .................................... A01N 43/38
(52) U.S. Cl. ............................ 504/138; 504/286
(58) Field of Search ...................... 504/286, 138

(56) References Cited

U.S. PATENT DOCUMENTS

| | | | |
|---|---|---|---|
| 3,442,818 | 5/1969 | Johnson | 252/353 |
| 4,973,352 | 11/1990 | Heinrich et al. | 71/91 |
| 5,045,105 | 9/1991 | Grossmann et al. | 71/74 |
| 5,062,884 | 11/1991 | Plath et al. | 71/95 |
| 5,543,385 | 8/1996 | Roechling et al. | 504/127 |

FOREIGN PATENT DOCUMENTS

| | | |
|---|---|---|
| 2018015 | 12/1990 | (CA) . |
| 2039001 | 9/1991 | (CA) . |
| 3603789 | 8/1987 | (DE) . |
| 240659 | 10/1987 | (EP) . |
| 330904 | 9/1989 | (EP) . |
| 385231 | 9/1990 | (EP) . |
| 400585 | 12/1990 | (EP) . |
| 413267 | 2/1991 | (EP) . |
| 449773 | 10/1991 | (EP) . |
| 654513 | 5/1995 | (EP) . |

OTHER PUBLICATIONS

Sato et al., *Agric. Biol. Chem.*, 55(11), 2677–81, 1991.

*Primary Examiner*—S. Mark Clardy

(57) ABSTRACT

A liquid formulation of cinidon-ethyl, i.e., ethyl (Z)-2-chloro-3-[2-chloro-5-(4,5,6,7-tetrahydro-1,3-dioxoisoindoledion-2-yl)phenyl] acrylate comprising, essentially, in addition to the above crop protection agent,
a) an ionic emulsifier,
b) a non-ionic emulsifier,
c) a non-nucleophilic and non-basic aromatic solvent and,
d) if desired, a further herbicidal crop protection agent, and a method of controlling undesirable vegetation using this formulation.

5 Claims, No Drawings

LIQUID FORMULATION OF ETHYL-(Z)-2-CHLORO-3-[2-CHLORO-5-(4,5,6,7-TETRAHYDRO-1,3-DIOXOISOINDOLEDION-2-YL)PHENYL]ACRYLATE

This application has been filed under 35 USC 371 as the national stage of international application PCT/EP97/04253, filed Aug. 5, 1997.

The present invention relates to a liquid formulation of ethyl (Z)-2-chloro-3-[2-chloro-5-(4,5,6,7-tetrahydro-1,3-dioxoisoindole ion-2-yl)phenyl]acrylate comprising, essentially, in addition to the above crop protection agent,
a) an ionic emulsifier,
b) a non-ionic emulsifier,
c) a non-nucleophilic and non-basic aromatic solvent and,
d) if desired, a further herbicidal crop protection agent.

The present invention furthermore relates to a method of controlling undesirable vegetation using this formulation.

EP-A 240 659 discloses the active ingredient ethyl (Z)-2-chloro-3-[2-chloro-5-(4,5,6,7-tetrahydro-1,3-dioxoisoindoledion-2-yl)-phenyl]acrylate for which "cinidon-ethyl" was proposed as common name. Furthermore, it can be seen clearly from this publication that the active ingredient is active against a series of dicotyledonous weeds under greenhouse conditions. However, the known formulations of this active ingredient are not completely satisfactory, in particular under field conditions.

Agric. Biol. Chem. 55 (11), (1991), pages 2677–2681 discloses that crop protection agents from the class of the N-aryl-3,4,5,6-tetrahydrophthalimides, for example the above cinidon-ethyl, may be subject to hydrolysis in the plant.

It is therefore an object of the present invention to provide a formulation of ethyl (Z)-2-chloro-3-[2-chloro-5-(4,5,6,7-tetrahydro-1,3-dioxoisoindoledion-2-yl)phenyl]acrylate in which this crop protection agent exerts a better biological activity combined with higher stability.

We have found that this object is achieved by the above-mentioned liquid formulation.

Moreover, we have found a method of controlling undesirable vegetation which utilizes this liquid formulation.

When preparing the formulation according to the invention, ethyl (Z)-2-chloro-3-[2-chloro-5-(4,5,6,7-tetrahydro-1,3-dioxoisoindoledion-2-yl)phenyl]acrylate is normally employed in a purity of from 80 to 100%.

This crop protection agent amounts normally to 5 to 50% by weight, in particular 10 to 30% by weight, of the liquid formulation according to the invention.

Especially suitable ionic emulsifiers are anionic surfactants, eg. alkali metal, alkaline earth metal or ammonium salts of the fatty acids, such as potassium stearate, alkyl sulfates, alkyl ether sulfates, alkyl- or iso-alkylsulfonates, alkylbenzenesulfonates such as sodium dodecylbenzenesulfonate and calcium dodecylbenzenesulfonate, alkylnaphthalenesulfonate, alkyl methyl ester sulfonates, acyl glutamates, alkylsuccinic ester sulfonates, sarcosinates such as sodium lauroyl sarcosinate and taurate. Mixtures of a plurality of these ionic emulsifiers are also suitable.

Preferred ionic emulsifiers are the salts of the alkylbenzenesulfonates and the alkylsulfosuccinates. Especially preferred ionic emulsifiers are the salts of alkylbenzenesulfonic acids, mainly calcium dodecylbenzenesulfonate and sodium dioctylsulfosuccinate, in particular calcium dodecylbezenesulfonate.

The ionic emulsifiers usually amount to from 2 to 20% by weight of the liquid formulation.

Suitable non-ionic emulsifiers are, for example, alkoxylated fats or oils of animal or vegetable origin such as maize oil ethoxylates, castor oil ethoxylates, tallow fat ethoxylates, glycerol esters such as glycerol monostearate, fatty alcohol alkoxylates and oxo-alcohol alkoxylates, fatty acid alkoxylates such as oleic acid ethoxylate, alkylphenyl alkoxylates such as isononyl-, isooctyl-, tributyl- and tristearylphenyl ethoxylates, fatty amine alkoxylates, fatty acid amide alkoxylates, sugar surfactants such as sorbitan fatty acid esters (sorbitan monooleate, sorbitan tristearate), polyoxyethylene sorbitan fatty acid esters, alkylpolyglycosides, N-alkylgluconamides, alkylmethyl sulfoxides, alkyldimethylphosphine oxides such as tetradecyldimethylphosphine oxide, and mixtures of such non-ionic emulsifiers.

Preferred non-ionic emulsifiers are ethoxylated or propoxylated naturally occurring carboxylic acids or alcohols, mainly ethoxylated oils such as castor oil ethoxylate having 36 to 50 ethylene oxide units.

The non-ionic emulsifiers in the liquid formulation normally amounts to from 2 to 20% by weight.

Suitable non-nucleophilic and non-basic aromatic solvents are cyclohexanone, halobenzenes such as chlorobenzene and liquid dichlorobenzenes, and also bromobenzene, alkylaromatics, preferably alkylbenzenes and alkylnaphthalenes whose alkyl groups have 1 to 20 carbon atoms, such as the Solvesso® series, eg. Solvesso® 100, Solvesso® 150 and Solvesso® 200 (Exxon Chemical) and mixtures of these, and methylbenzenes: toluene, o-xylene, m-xylene, p-xylene; ethylbenzene; iso-propylbenzene; tert-butylbenzene.

Mixtures of these are also suitable.

Preferred non-nucleophilic and non-basic aromatic solvents are Shellsol® products (Deutsche Shell Chemie GmbH) or Solvesso® products: Solvesso® 100, Solvesso® 150, Solvesso® 200, in particular Solvesso® 200.

The solvent generally amounts to so much of the liquid formulation that the total of all components is 100% by weight.

The liquid formulations according to the invention may additionally comprise other active ingredients conventionally used in crop protection, eg. other herbicidally, fungicidally and insecticidally active or growth-regulating active ingredients.

Herbicidal crop protection agents which are preferred as further active ingredients conventionally used in crop protection are those from the group below: ethyl 2-chloro-3-[2-chloro-4-fluoro-5-(4-difluoromethyl-4,5-dihydro-3-methyl-5-oxo-1H-1,2,4-triazol-1-yl)phenyl]propionate (F8426), diflufenzopyr, dimethenamid, flamprop-methyl, propanil, aryloxyalkanecarboxylic acids and their esters such as 2,4-D, 2,4-DB, dichlorprop, dichlorprop-P (2,4-DP-P), MCPA, MCPB, mecoprop, mecoprop-P and [(4-amino-3,5-dichloro-6-fluoro-2-pyridyl)oxy]acetic acid (fluroxypyr), benzoic acids such as chloramben, dicamba, benzothiadiazinones such as bentazone, bleachers such as clomazone (dimethazone), diflufenican, fluorochloridone, flupoxam, fluridone, pyrazolate, sulcotrione (chlormesulone), carbamates such as carbetamide, chlorbufam, chlorpropham, desmedipham, phenmedipham, vernolate, quinolinecarboxylic acids such as quinclorac, quinmerac, dinitroanilines such as butralin, fluchloralin, isopropalin, nitralin, oryzalin, pendimethalin, prodiamine, profluralin, trifluralin, dinitrophenols such as bromofenoxim, dinoseb, dinoseb-acetate, dinoterb, DNOC, minoterb-acetate, diphenyl ethers such as acifluorfen-sodium, aclonifen, bifenox, chlornitrofen (CNP), difenoxuron, ethoxyfen, fluorodifen, fluoroglycofen-ethyl, fomesafen, furyloxyfen, lactofen, nitrofen, nitrofluorfen, oxyfluorfen, phenols such as bromoxynil, ioxynil, phenoxyphenoxypropionic esters such as clodinafop, cyhalofop-butyl, diclofop-methyl, fenoxaprop-ethyl, fenoxaprop-p-ethyl, fenthiapropethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofop-tefuryl, pyridazines such as chloridazon, maleic hydrazide, norflurazon, pyridate, pyridinecarboxylic acids such as clopytalid, dithiopyr, picloram, thiazopyr, uracils such as bromacil, lenacil, terbacil and crop protection agents of the cyclohexanone type such as sethoxydim, cycloxydim, clethodim, tralkoxydim, butroxydim, 2-(1-(3-chloroallyloxy)iminopropyl)-5-(tetrahydropyran-4-yl)-3-hydroxycyclohex-2-enone and 2-(1-(2-p-chlorophenoxypropyloxy)-iminobutyl-5-(tetrahydrothiopyran-3-yl)-3-hydroxycyclohex-2-enone.

Herbicidal crop protection agents which are especially preferred as further active ingredients conventionally used in crop protection are those from the group below: ethyl 2-chloro-3-[2-chloro-4-fluoro-5-(4-difloromethyl-4,5-dihydro-3-methyl-5-oxo-1H-1,2,4-triazol-1-yl)phenyl] propionate (F8426), dimetheneamid, dinitroanilines such as pendimethalin, crop protection agents of the cyclohexenone type such as sethoxydim, cycloxydim, clethodim, tralkoxydim, butroxydim, 2-(1-(3-chloroallyloxy)-iminopropyl)-5-(tetrahydropyran-4-yl)-3-hydroxy-cyclohex-2-enone and 2-(1-(2-p-chlorophenoxypropyloxy)-iminobutyl-5-(tetrahydrothiopyran-3-yl)-3-hydroxy-cyclohex-2-enone, furthermore aryloxyalkanecarboxylic acids such as 2,4-D, 2,4-DB, CMPP, CMPP-P, dichlorprop, dichlorprop-P, MCPA, MCPB, the esters of these compounds, in particular the isopropyl, butyl and isooctyl esters, mainly the 2-ethylhexyl esters and [(4-amino-3,5-dichloro-6-fluoro-2-pyridyl)oxy]acetic acid (fluroxypyr).

Very especially preferred components d) in the mixture are F8426, dimetheneamid, pendimethalin, the isooctyl ester of 2,4-D, and fluroxypyr. These further active ingredients normally amount to 0 to 80 and preferably 10 to 70% by weight based on the weight of the finished formulation.

In addition, the liquid formulations according to the invention can comprise other conventional additives such as antifoams and cosolvents and the like.

Antifoams which are suitable are, for example, aliphatic or aromatic monoalcohols having 4 to 14, preferably 6 to 10, carbon atoms, such as n-octanol or n-decanol, or silicone surfactants.

The antifoams normally amount to from 0 to 10 and mainly from 0.01 to 1% by weight in the formulation.

Suitable cosolvents are in particular mineral oils, naturally occurring oils such as rapeseed oil, soya oil and the methyl esters of the carboxylic acids on which these oils are based, such as methyl oleate and rapeseed oil methyl ester, fatty acid esters, mainly with $C_1$-$C_4$-alkanols.

The liquid formulation according to the invention is prepared in a manner known per se by mixing the components, if appropriate with stirring and/or heating.

The products thus obtainable are normally homogeneous emulsion concentrates.

Containers which are suitable for the formulations are all containers conventionally used for crop protection products, mainly bottles, canisters, and bags made of chemical-resistant polymers. The use of water-soluble containers, mainly water-soluble film bags, in particular based on polyvinyl alcohol.

The application of such spray mixtures for controlling undesirable vegetation, where it is allowed to act on the crop plant, its environment and/or its seed, is sufficiently well known to those skilled in the art, so that any further information is unnecessary.

It has been found that cinidon-ethyl in the liquid formulations according to the invention is considerably more stable in the absence of basic substances.

EXAMPLES

Preparation Example 1

200 g of cinidon-ethyl, 40 g of calcium dodecylbenzenesulfonate salt (eg. Wettol® EM 1, BASF AG), 60 g of a castor oil ethoxylate reacted with 48 mol of ethylene oxide (eg. Wettol® EM 31, BASF AG) were mixed in approximately 740 ml of Solvesso® 200 (Exxon Chemical) with stirring, whereby an emulsion concentrate comprising 200 g of active ingredient/l was obtained.

The value (%) to which the cinidon-ethyl content of the resulting formulation dropped over a period of 1 to 2 years was determined at a range of storage temperatures. Table 1 shows the averages of in each case 24 storage trials.

| Storage time | 20° C. | 30° C. | 40° C. | 50° C. |
|---|---|---|---|---|
| 1 year | 99.6 | 99.2 | 98.9 | 98.2 |
| 2 years | 98.7 | 98.1 | 97.5 | 95.4 |

Preparation Example 2 (Comparison Example)

50% by weight of cinidon-ethyl, 10% by weight of a phenylsulfonic acid/formaldehyde condensate (eg. Wettol® D1, BASF AG), 3% by weight of a condensate of phenol, formaldehyde and sodium sulfite (eg. Wettol® SSP, BASF AG), 5% by weight of sodium dialkylnaphthalenesulfonate (eg. Wettol® NT 1, BASF AG), 10% by weight of highly-disperse silica (eg. Sipernat® 22, Degussa) and 22% by weight of kaolin were mixed intimately, and the mixture was ground twice using a pinned-disk mill and again mixed. This gave a wettable powder whose stability as a suspension was sufficiently high and which had good wetting properties.

Preparation Example 3

50 g/l cinidon-ethyl, 420 g/l isooctyl ester of 2,4-D, 50 g/l Wettol® EM 1 and 50 g/l Wettol® EM 31 were mixed in Solvesso® 200 (Exxon Chemical) to give a homogeneous emulsion concentrate.

Use Examples

The formulation according to the invention of Preparation Example 1 was compared with the comparison formulation (Preparation Example 2) in a spring treatment of cereals. In small-plot trials (plot size: 10 m²), the stated amount of herbicide in 250 l of water/ha was applied, by means of a self-propelled sprayer, when the crop plants had reached a growth stage of 21–29. Table 2 shows the percentage destruction rates of a variety of weeds achieved with a rate of application of 50 g/ha of cinidon-ethyl.

TABLE 2

| Weed | Formulation of Preparation Example 1 | Formulation of Preparation Example 2 |
|---|---|---|
| Galium aparine | 100 | 13 |
| Papaver rhoeas | 47 | 0 |
| Veronica hederaefolia | 76 | 0 |
| Stellaria media | 47 | 0 |

The data found with a rate of application of 100 g of cinidon-ethyl per ha are compiled in Table 3:

TABLE 3

| Weed | Formulation of Preparation Example 1 | Formulation of Preparation Example 2 |
|---|---|---|
| Galium aparine | 96 | 76 |
| Papaver rhoeas | 71 | 38 |
| Veronica hederaefolia | 81 | 47 |
| Stellaria media | 72 | 37 |

The above experiments reveal that the liquid formulation according to the invention in accordance with Preparation Example 1 is considerably more effective against undesirable vegetation than the wettable powder in accordance with Preparation Example 2.

Stability Test

Various amounts of N-propylamine or acetic acid were added to a formulation of 200 g/l cinidon-ethyl and 100 g/l emulsifier mixture (made with 40 g/l Wettol® EM 1 and 60 g/l Wettol® EM 31) in Solvesso® 200, and the content of crop protection agent was determined after 6 and 30 days, respectively (initial content: 100%). The results can be seen from Table 4 ("n.d."=not detectable).

TABLE 4

| | | Content of active ingredient after ... [%] | |
|---|---|---|---|
| Additive | pH | 6 days | 30 days |
| 20 g/l N-propylamine | 7.5 | 37 | n.d. |
| 5 g/l N-propylamine | 7.2 | 85 | n.d. |
| 0.3 g/l N-propylamine | 6.6 | 100 | 100 |
| no additive | 5.2 | 100 | 100 |
| 20 g/l acetic acid | 4.4 | 100 | 100 |

It can clearly be seen that even small amounts of the base N-propylamine reduce the stability of cinidon-ethyl, while acids such as acetic acid have no such effect.

We claim:

1. A liquid formulation of ethyl (Z)-2-chloro-3-[2-chloro-5-(4,5,6,7-tetrahydro-1,3-dioxoisoindoledion-2-yl)phenyl]-acrylate comprising, essentially, in addition to the above crop protection agent, a) an ionic emulsifier, b) a non-ionic emulsifer, c) a non-nucleophilic and non-basic aromatic solvent and, d) if desired, a further herbicidal crop protection agent.

2. A formulation as claimed in claim 1 which comprises, as ionic emulsifier, the salt of an alkylbenzenesulfonic acid.

3. A formulation as claimed in claim 1 which comprises, as non-ionic emulsifier, an ethoxylated or propoxylated naturally occurring carboxylic acid or an ethoxylated or propoxylated naturally occurring alcohol.

4. A formulation as claimed in claim 1 which comprises as further herbicidal crop protection agent one or more crop protection agents selected from the following group: aryloxyalkanecarboxylic acids, dinitroanilines, active ingredients of the cyclohexenone type.

5. A method of controlling undesirable vegetation, which comprises allowing a formulation as claimed in claim 1 to act on crop plants, their environment and/or their seed.

* * * * *

UNITED STATES PATENT AND TRADEMARK OFFICE
CERTIFICATE OF CORRECTION

PATENT NO. : 6,225,259 B1
DATED : May 1, 2001
INVENTOR(S) : Berghaus et al.

It is certified that error appears in the above-identified patent and that said Letters Patent is hereby corrected as shown below:

Insert the following assignee information on the title page of the patent:

--(73) Assignee: BASF Aktiengesellschaft
       Ludwigshafen (DE)--

Signed and Sealed this

Fourteenth Day of August, 2001

*Attest:*

NICHOLAS P. GODICI
*Attesting Officer*  Acting Director of the United States Patent and Trademark Office